(12) United States Patent
Wilson et al.

(10) Patent No.: US 9,384,329 B2
(45) Date of Patent: Jul. 5, 2016

(54) CALORIC BURN DETERMINATION FROM BODY MOVEMENT

(75) Inventors: Andrew Wilson, Leics (GB); Mark Stevenson, Warwickshire (GB); Nicholas Burton, Derby (GB); William Bryan, Leicestershire (GB); James Thomas, Warwickshire (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 633 days.

(21) Appl. No.: 12/813,702

(22) Filed: Jun. 11, 2010

(65) Prior Publication Data
US 2011/0306468 A1   Dec. 15, 2011

(51) Int. Cl.
*G06K 9/00* (2006.01)
*G06F 19/00* (2011.01)

(52) U.S. Cl.
CPC ................................ *G06F 19/3475* (2013.01)

(58) Field of Classification Search
None
See application file for complete search history.

(56) References Cited

U.S. PATENT DOCUMENTS

| | | | |
|---|---|---|---|
| 4,627,620 A | 12/1986 | Yang | |
| 4,630,910 A | 12/1986 | Ross et al. | |
| 4,645,458 A | 2/1987 | Williams | |
| 4,695,953 A | 9/1987 | Blair et al. | |
| 4,702,475 A | 10/1987 | Elstein et al. | |
| 4,711,543 A | 12/1987 | Blair et al. | |
| 4,751,642 A | 6/1988 | Silva et al. | |
| 4,796,997 A | 1/1989 | Svetkoff et al. | |
| 4,809,065 A | 2/1989 | Harris et al. | |
| 4,817,950 A | 4/1989 | Goo | |
| 4,843,568 A | 6/1989 | Krueger et al. | |
| 4,893,183 A | 1/1990 | Nayar | |
| 4,901,362 A | 2/1990 | Terzian | |
| 4,925,189 A | 5/1990 | Braeunig | |
| 5,101,444 A | 3/1992 | Wilson et al. | |
| 5,148,154 A | 9/1992 | MacKay et al. | |
| 5,184,295 A | 2/1993 | Mann | |
| 5,228,078 A | 7/1993 | Bitzmann | |
| 5,229,754 A | 7/1993 | Aoki et al. | |
| 5,229,756 A | 7/1993 | Kosugi et al. | |
| 5,239,463 A | 8/1993 | Blair et al. | |
| 5,239,464 A | 8/1993 | Blair et al. | |
| 5,288,078 A | 2/1994 | Capper et al. | |

(Continued)

FOREIGN PATENT DOCUMENTS

| CN | 101068605 | 11/2007 |
|---|---|---|
| CN | 101254344 B | 6/2010 |

(Continued)

OTHER PUBLICATIONS

Toyama, Kentaro, et al., "Probabilistic Tracking in a Metric Space," Eighth International Conference on Computer Vision, Vancouver, Canada, vol. 2, Jul. 2001, 8 pages.

(Continued)

*Primary Examiner* — Nancy Bitar
(74) *Attorney, Agent, or Firm* — Gregg Wisdom; Judy Yee; Micky Minhas

(57) ABSTRACT

A system and method is disclosed determining caloric burn via an HCI system. Using a capture device which is able to detect the thickness of a user's arms, legs, torso, etc., the system determines a mass for each of a user's body parts. Thereafter, in one example, the system measures caloric burn for a given body part as a function of how far the body part was displaced, a mass of the body part displaced and gravity.

23 Claims, 10 Drawing Sheets

(56) References Cited

U.S. PATENT DOCUMENTS

| | | |
|---|---|---|
| 5,295,491 A | 3/1994 | Gevins |
| 5,320,538 A | 6/1994 | Baum |
| 5,347,306 A | 9/1994 | Nitta |
| 5,385,519 A | 1/1995 | Hsu et al. |
| 5,405,152 A | 4/1995 | Katanics et al. |
| 5,417,210 A | 5/1995 | Funda et al. |
| 5,423,554 A | 6/1995 | Davis |
| 5,454,043 A | 9/1995 | Freeman |
| 5,469,740 A | 11/1995 | French et al. |
| 5,495,576 A | 2/1996 | Ritchey |
| 5,516,105 A | 5/1996 | Eisenbrey et al. |
| 5,524,637 A | 6/1996 | Erickson |
| 5,534,917 A | 7/1996 | MacDougall |
| 5,563,988 A | 10/1996 | Maes et al. |
| 5,577,981 A | 11/1996 | Jarvik |
| 5,580,249 A | 12/1996 | Jacobsen et al. |
| 5,594,469 A | 1/1997 | Freeman et al. |
| 5,597,309 A | 1/1997 | Riess |
| 5,616,078 A | 4/1997 | Oh |
| 5,617,312 A | 4/1997 | Iura et al. |
| 5,638,300 A | 6/1997 | Johnson |
| 5,641,288 A | 6/1997 | Zaenglein |
| 5,682,196 A | 10/1997 | Freeman |
| 5,682,229 A | 10/1997 | Wangler |
| 5,690,582 A | 11/1997 | Ulrich et al. |
| 5,703,367 A | 12/1997 | Hashimoto et al. |
| 5,704,837 A | 1/1998 | Iwasaki et al. |
| 5,715,834 A | 2/1998 | Bergamasco et al. |
| 5,875,108 A | 2/1999 | Hoffberg et al. |
| 5,877,803 A | 3/1999 | Wee et al. |
| 5,913,727 A | 6/1999 | Ahdoot |
| 5,933,125 A | 8/1999 | Fernie |
| 5,980,256 A | 11/1999 | Carmein |
| 5,989,157 A | 11/1999 | Walton |
| 5,995,649 A | 11/1999 | Marugame |
| 6,005,548 A | 12/1999 | Latypov et al. |
| 6,009,210 A | 12/1999 | Kang |
| 6,054,991 A | 4/2000 | Crane et al. |
| 6,066,075 A | 5/2000 | Poulton |
| 6,072,494 A | 6/2000 | Nguyen |
| 6,073,489 A | 6/2000 | French et al. |
| 6,077,201 A | 6/2000 | Cheng et al. |
| 6,098,458 A | 8/2000 | French et al. |
| 6,100,896 A | 8/2000 | Strohecker et al. |
| 6,101,289 A | 8/2000 | Kellner |
| 6,128,003 A | 10/2000 | Smith et al. |
| 6,130,677 A | 10/2000 | Kunz |
| 6,141,463 A | 10/2000 | Covell et al. |
| 6,147,678 A | 11/2000 | Kumar et al. |
| 6,152,856 A | 11/2000 | Studor et al. |
| 6,159,100 A | 12/2000 | Smith |
| 6,173,066 B1 | 1/2001 | Peurach et al. |
| 6,181,343 B1 | 1/2001 | Lyons |
| 6,188,777 B1 | 2/2001 | Darrell et al. |
| 6,215,890 B1 | 4/2001 | Matsuo et al. |
| 6,215,898 B1 | 4/2001 | Woodfill et al. |
| 6,226,396 B1 | 5/2001 | Marugame |
| 6,229,913 B1 | 5/2001 | Nayar et al. |
| 6,256,033 B1 * | 7/2001 | Nguyen .............. 715/863 |
| 6,256,400 B1 | 7/2001 | Takata et al. |
| 6,283,860 B1 | 9/2001 | Lyons et al. |
| 6,289,112 B1 | 9/2001 | Jain et al. |
| 6,299,308 B1 | 10/2001 | Voronka et al. |
| 6,308,565 B1 | 10/2001 | French et al. |
| 6,316,934 B1 | 11/2001 | Amorai-Moriya et al. |
| 6,363,160 B1 | 3/2002 | Bradski et al. |
| 6,384,819 B1 | 5/2002 | Hunter |
| 6,411,744 B1 | 6/2002 | Edwards |
| 6,430,997 B1 | 8/2002 | French et al. |
| 6,476,834 B1 | 11/2002 | Doval et al. |
| 6,496,598 B1 | 12/2002 | Harman |
| 6,503,195 B1 | 1/2003 | Keller et al. |
| 6,527,674 B1 | 3/2003 | Clem |
| 6,539,931 B2 | 4/2003 | Trajkovic et al. |
| 6,570,555 B1 | 5/2003 | Prevost et al. |
| 6,633,294 B1 | 10/2003 | Rosenthal et al. |
| 6,640,202 B1 | 10/2003 | Dietz et al. |
| 6,661,918 B1 | 12/2003 | Gordon et al. |
| 6,681,031 B2 | 1/2004 | Cohen et al. |
| 6,714,665 B1 | 3/2004 | Hanna et al. |
| 6,731,799 B1 | 5/2004 | Sun et al. |
| 6,738,066 B1 | 5/2004 | Nguyen |
| 6,765,726 B2 | 7/2004 | French et al. |
| 6,788,809 B1 | 9/2004 | Grzeszczuk et al. |
| 6,801,637 B2 | 10/2004 | Voronka et al. |
| 6,873,723 B1 | 3/2005 | Aucsmith et al. |
| 6,876,496 B2 | 4/2005 | French et al. |
| 6,937,742 B2 | 8/2005 | Roberts et al. |
| 6,950,534 B2 | 9/2005 | Cohen et al. |
| 7,003,134 B1 | 2/2006 | Covell et al. |
| 7,036,094 B1 | 4/2006 | Cohen et al. |
| 7,038,855 B2 | 5/2006 | French et al. |
| 7,039,676 B1 | 5/2006 | Day et al. |
| 7,042,440 B2 | 5/2006 | Pryor et al. |
| 7,047,547 B2 * | 5/2006 | Alten et al. .............. 725/28 |
| 7,050,606 B2 | 5/2006 | Paul et al. |
| 7,058,204 B2 | 6/2006 | Hildreth et al. |
| 7,060,957 B2 | 6/2006 | Lange et al. |
| 7,113,918 B1 | 9/2006 | Ahmad et al. |
| 7,121,946 B2 | 10/2006 | Paul et al. |
| 7,170,492 B2 | 1/2007 | Bell |
| 7,184,048 B2 | 2/2007 | Hunter |
| 7,202,898 B1 | 4/2007 | Braun et al. |
| 7,222,078 B2 | 5/2007 | Abelow |
| 7,227,526 B2 | 6/2007 | Hildreth et al. |
| 7,259,747 B2 | 8/2007 | Bell |
| 7,308,112 B2 | 12/2007 | Fujimura et al. |
| 7,317,836 B2 | 1/2008 | Fujimura et al. |
| 7,348,963 B2 | 3/2008 | Bell |
| 7,359,121 B2 | 4/2008 | French et al. |
| 7,367,887 B2 * | 5/2008 | Watabe et al. .............. 463/36 |
| 7,379,563 B2 | 5/2008 | Shamaie |
| 7,379,566 B2 | 5/2008 | Hildreth |
| 7,389,591 B2 | 6/2008 | Jaiswal et al. |
| 7,412,077 B2 | 8/2008 | Li et al. |
| 7,421,093 B2 | 9/2008 | Hildreth et al. |
| 7,430,312 B2 | 9/2008 | Gu |
| 7,436,496 B2 | 10/2008 | Kawahito |
| 7,450,736 B2 | 11/2008 | Yang et al. |
| 7,452,275 B2 | 11/2008 | Kuraishi |
| 7,460,690 B2 | 12/2008 | Cohen et al. |
| 7,489,812 B2 | 2/2009 | Fox et al. |
| 7,536,032 B2 | 5/2009 | Bell |
| 7,552,031 B2 | 6/2009 | Vock et al. |
| 7,555,142 B2 | 6/2009 | Hildreth et al. |
| 7,560,701 B2 | 7/2009 | Oggier et al. |
| 7,570,805 B2 | 8/2009 | Gu |
| 7,574,020 B2 | 8/2009 | Shamaie |
| 7,576,727 B2 | 8/2009 | Bell |
| 7,590,262 B2 | 9/2009 | Fujimura et al. |
| 7,593,552 B2 | 9/2009 | Higaki et al. |
| 7,598,942 B2 | 10/2009 | Underkoffler et al. |
| 7,607,509 B2 | 10/2009 | Schmiz et al. |
| 7,620,202 B2 | 11/2009 | Fujimura et al. |
| 7,668,340 B2 | 2/2010 | Cohen et al. |
| 7,680,298 B2 | 3/2010 | Roberts et al. |
| 7,683,954 B2 | 3/2010 | Ichikawa et al. |
| 7,684,592 B2 | 3/2010 | Paul et al. |
| 7,701,439 B2 | 4/2010 | Hillis et al. |
| 7,702,130 B2 | 4/2010 | Im et al. |
| 7,704,135 B2 | 4/2010 | Harrison, Jr. |
| 7,710,391 B2 | 5/2010 | Bell et al. |
| 7,729,530 B2 | 6/2010 | Antonov et al. |
| 7,746,345 B2 | 6/2010 | Hunter |
| 7,760,182 B2 | 7/2010 | Ahmad et al. |
| 7,809,167 B2 | 10/2010 | Bell |
| 7,834,846 B2 | 11/2010 | Bell |
| 7,852,262 B2 | 12/2010 | Namineni et al. |
| RE42,256 E | 3/2011 | Edwards |
| 7,898,522 B2 | 3/2011 | Hildreth et al. |
| 7,959,567 B2 * | 6/2011 | Stivoric et al. .............. 600/300 |
| 8,035,612 B2 | 10/2011 | Bell et al. |
| 8,035,614 B2 | 10/2011 | Bell et al. |
| 8,035,624 B2 | 10/2011 | Bell et al. |

(56) References Cited

U.S. PATENT DOCUMENTS

| | | | |
|---|---|---|---|
| 8,072,470 B2 | 12/2011 | Marks | |
| 8,379,919 B2* | 2/2013 | Bronder et al. | 382/103 |
| 8,613,666 B2* | 12/2013 | Esaki et al. | 463/39 |
| 8,702,485 B2* | 4/2014 | Flury | A63F 13/10 463/34 |
| 8,957,890 B2* | 2/2015 | Yamamoto | 345/419 |
| 2004/0005924 A1 | 1/2004 | Watabe et al. | 463/36 |
| 2008/0026838 A1 | 1/2008 | Dunstan et al. | |
| 2008/0275309 A1 | 11/2008 | Stivoric et al. | |
| 2009/0048044 A1 | 2/2009 | Oleson et al. | |
| 2009/0054209 A1 | 2/2009 | Takeishi et al. | |
| 2009/0117958 A1* | 5/2009 | Ueshima | A63F 13/10 463/8 |
| 2009/0133051 A1* | 5/2009 | Hildreth | 725/28 |
| 2009/0221936 A1 | 9/2009 | Levine et al. | |
| 2009/0233770 A1 | 9/2009 | Vincent et al. | |
| 2011/0185309 A1* | 7/2011 | Challinor | A63F 13/10 715/784 |
| 2011/0281249 A1* | 11/2011 | Gammell | A63B 24/0075 434/247 |
| 2011/0306396 A1* | 12/2011 | Flury et al. | 463/7 |
| 2012/0143358 A1* | 6/2012 | Adams | A63F 13/10 700/92 |

FOREIGN PATENT DOCUMENTS

| | | |
|---|---|---|
| EP | 0583061 A2 | 2/1994 |
| JP | 08044490 A1 | 2/1996 |
| JP | 4006949 | 11/2001 |
| WO | 93/10708 A1 | 6/1993 |
| WO | 97/17598 A1 | 5/1997 |
| WO | 99/44698 A1 | 9/1999 |
| WO | 2004002593 | 1/2004 |

OTHER PUBLICATIONS

Buttussi, "Bringing Mobile Guides and Fitness Activities Together: A Solution Based on an Embodied Virtual Trainer", ACM International Conference Proceeding Series, Proceedings of the 8th Conference on Human-Computer Interaction with Mobile Devices and Services, Sep. 12-15, 2006, pp. 29-36, ACM, New York, NY, USA.

Ching, "Fitness Monitor System", Conference on Convergent Technologies for Asia-Pacific Region, Oct. 15-17, 2003, pp. 1399-1403, IEEE Publishers.

Marshall, "Mapping Children's Places and Activities: Analysis of the Local Area Around a Primary School", International Conference on Planning and Designing Healthy Public Outdoor Spaces for Young People in the 21st Century, Jul. 2006, 20 pages, Bristol, UK.

Kanade et al., "A Stereo Machine for Video-rate Dense Depth Mapping and Its New Applications", IEEE Computer Society Conference on Computer Vision and Pattern Recognition, 1996, pp. 196-202, The Robotics Institute, Carnegie Mellon University, Pittsburgh, PA.

Miyagawa et al., "CCD-Based Range Finding Sensor", Oct. 1997, pp. 1648-1652, vol. 44 No. 10, IEEE Transactions on Electron Devices.

Rosenhahn et al., "Automatic Human Model Generation", 2005, pp. 41-48, University of Auckland (CITR), New Zealand.

Aggarwal et al., "Human Motion Analysis: A Review", IEEE Non-rigid and Articulated Motion Workshop, 1997, University of Texas at Austin, Austin, TX.

Shao et al., "An Open System Architecture for a Multimedia and Multimodal User Interface", Aug. 24, 1998, Japanese Society for Rehabilitation of Persons with Disabilities (JSRPD), Japan.

Kohler, "Special Topics of Gesture Recognition Applied in Intelligent Home Environments", In Proceedings of the Gesture Workshop, 1998, pp. 285-296, Germany.

Kohler, "Vision Based Remote Control in Intelligent Home Environments", University of Erlangen-Nuremberg/Germany, 1996, pp. 147-154, Germany.

Kohler, "Technical Details and Ergonomical Aspects of Gesture Recognition applied in Intelligent Home Environments", 1997, Germany.

Hasegawa et al., "Human-Scale Haptic Interaction with a Reactive Virtual Human in a Real-Time Physics Simulator", Jul. 2006, vol. 4, No. 3, Article 6C, ACM Computers in Entertainment, New York, NY.

Qian et al., "A Gesture-Driven Multimodal Interactive Dance System", Jun. 2004, pp. 1579-1582, IEEE International Conference on Multimedia and Expo (ICME), Taipei, Taiwan.

Zhao, "Dressed Human Modeling, Detection, and Parts Localization", 2001, The Robotics Institute, Carnegie Mellon University, Pittsburgh, PA.

He, "Generation of Human Body Models", Apr. 2005, University of Auckland, New Zealand.

Isard et al., "Condensation—Conditional Density Propagation for Visual Tracking", 1998, pp. 5-28, International Journal of Computer Vision 29(1), Netherlands.

Livingston, "Vision-based Tracking with Dynamic Structured Light for Video See-through Augmented Reality", 1998, University of North Carolina at Chapel Hill, North Carolina, USA.

Wren et al., "Pfinder: Real-Time Tracking of the Human Body", MIT Media Laboratory Perceptual Computing Section Technical Report No. 353, Jul. 1997, vol. 19, No. 7, pp. 780-785, IEEE Transactions on Pattern Analysis and Machine Intelligence, Caimbridge, MA.

Breen et al., "Interactive Occlusion and Collision of Real and Virtual Objects in Augmented Reality", Technical Report ECRC-95-02, 1995, European Computer-Industry Research Center GmbH, Munich, Germany.

Freeman et al., "Television Control by Hand Gestures", Dec. 1994, Mitsubishi Electric Research Laboratories, TR94-24, Caimbridge, MA.

Hongo et al., "Focus of Attention for Face and Hand Gesture Recognition Using Multiple Cameras", Mar. 2000, pp. 156-161, 4th IEEE International Conference on Automatic Face and Gesture Recognition, Grenoble, France.

Pavlovic et al., "Visual Interpretation of Hand Gestures for Human-Computer Interaction: A Review", Jul. 1997, pp. 677-695, vol. 19, No. 7, IEEE Transactions on Pattern Analysis and Machine Intelligence.

Azarbayejani et al., "Visually Controlled Graphics", Jun. 1993, vol. 15, No. 6, IEEE Transactions on Pattern Analysis and Machine Intelligence.

Granieri et al., "Simulating Humans in VR", The British Computer Society, Oct. 1994, Academic Press.

Brogan et al., "Dynamically Simulated Characters in Virtual Environments", Sep./Oct. 1998, pp. 2-13, vol. 18, Issue 5, IEEE Computer Graphics and Applications.

Fisher et al., "Virtual Environment Display System", ACM Workshop on Interactive 3D Graphics, Oct. 1986, Chapel Hill, NC.

"Virtual High Anxiety", Tech Update, Aug. 1995, pp. 22.

Sheridan et al., "Virtual Reality Check", Technology Review, Oct. 1993, pp. 22-28, vol. 96, No. 7.

Stevens, "Flights into Virtual Reality Treating Real World Disorders", The Washington Post, Mar. 27, 1995, Science Psychology, 2 pages.

"Simulation and Training", 1994, Division Incorporated.

English Machine-translation of Japanese Publication No. JP08-044490 published on Feb. 16, 1996.

Voluntary Amendments filed Mar. 21, 2012 in Chinese Patent Application No. 201110168386.3.

English translation of claims as amended in Voluntary Amendments filed Mar. 21, 2012 in Chinese Patent Application No. 201110168386.3.

First Office Action dated Aug. 27, 2013 in Chinese Patent Application No. 201110168386.3.

English language translation and Summary of First Office Action dated Aug. 27, 2013 in Chinese Patent Application No. 201110168386.3.

Second Office Action dated May 9, 2014 in Chinese Patent Application No. 201110168386.3.

Partial English language translation of Second Office Action dated May 9, 2014 in Chinese Patent Application No. 201110168386.3.

Response to First Office Action filed Jan. 10, 2014 in Chinese Patent Application No. 201110168386.3.

(56) References Cited

OTHER PUBLICATIONS

Partial English language translation of Response to First Office Action and English translation of amended claims filed Jan. 10, 2014 in Chinese Patent Application No. 201110168386.3.
Third Office Action dated Nov. 15, 2014, and partial English translation thereof, in Chinese Application No. 201110168386.3.
Response to Second Office Action filed Jul. 24, 2014 in Chinese Patent Application No. 201110168386.3.
English Summary and Claims as Amended in Response to Second Office Action filed Jul. 24, 2014 in Chinese Patent Application No. 201110168386.3.
"Final Office Action Issued in Chinese Patent Application No. 201110168386.3", Mailed Date: Nov. 20, 2015, 8 Pages.

* cited by examiner

CALORIC BURN DETERMINATION FROM BODY MOVEMENT

BACKGROUND

In the past, computing applications such as computer games and multimedia applications used controllers, remotes, keyboards, mice, or the like to allow users to manipulate game characters or other aspects of an application. More recently, computer games and multimedia applications have begun employing cameras and software gesture recognition engines to provide a human computer interface ("HCI"). With HCI, user gestures are detected, interpreted and used to control game characters or other aspects of an application.

Conventional HCI systems have not been used to measure caloric burn. Typically, caloric burn may be measured by conventional exercise equipment indirectly and mechanically. In particular, a user performs some work on a piece of equipment which is calibrated to determine caloric burn based on the amount of work performed on the equipment. These systems do not measure caloric burn of the person directly. Moreover, such systems typically do not measure work performed by a user unless the user sets the equipment in motion. Thus, even though a user may be performing work and burning calories while standing still, this work is not measured by the equipment.

SUMMARY

Disclosed herein are systems and methods for determining caloric burn via an HCI system. Using a capture device which is able to detect the thickness of a user's arms, legs torso, etc., the system determines a mass for each of a user's body parts. Thereafter, in one embodiment, the system measures caloric burn for a given body part as a function of how far the body part was displaced, a mass of the body part displaced and gravity. In a straightforward embodiment, the system may only measure upward vertical displacement as factoring into caloric burn. In further embodiments, the system may measure caloric burn as a function of upward vertical displacement, horizontal displacement and/or downward vertical displacement, and all combinations of such displacement. In further embodiments, the system may also measure caloric burn due to holding a body part stationary at some non-neutral position. In such embodiments, the system may measure caloric burn due to such stationary, non-neutral position as a function of the potential energy stored in the body part.

In one embodiment, the current technology relates to a method of determining caloric burn of a user, by capturing an image of a body part of a user via a capture device; determining a mass of the body part via a processor of a computing environment; capturing a movement of the body part via the capture device; and determining calories burned by the body part due to the captured movement of the body part and the determined mass of the body part.

In a further embodiment, the current technology relates to a system including a capture device capable of capturing an image of one or more discrete body parts of a user as the user moves within a field of view of the capture device; and a computing environment associated with the capture device, the computing environment including a processor capable of determining a mass of the one or more discrete body parts captured by the capture device, and determining calories burned by the one or more discrete body parts due to the determined mass of the one or more discrete body parts and a direction and degree of movement of the one or more discrete body parts.

In a further embodiment, the current technology relates to a system for facilitating weight loss, including a capture device capable of capturing an image of one or more discrete body parts of a user as the user moves within a field of view of the capture device; a computing environment associated with the capture device, the computing environment including determining a mass of the one or more discrete body parts captured by the capture device, and determining calories burned by the one or more discrete body parts due to the determined mass of the one or more discrete body parts and a direction and degree of movement of the one or more discrete body parts, the processor further running an exercise program; and a display associated with the computing environment, the display prompting a user to perform exercises per the exercise program run by the processor, the display further displaying the calories burned as determined by the processor.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure.

DETAILED DESCRIPTION

Embodiments of the present technology will now be described with reference to FIGS. 1A-11, which in general relate to a system for measuring caloric burn by detecting position and/or movement of a user via a human computer interface and determining caloric burn therefrom. In embodiments, the present system makes a determination as to skeletal mass and measures a position of skeletal joints, such as elbow, wrist, knee and ankle. The system then determines calories burned by the user based on the determined mass and joint position relative to a reference position. In further embodiments, the system may factor in other kinesthetic parameters such as velocity, and may use other body parts for the caloric burn measurement.

Figure 1A:
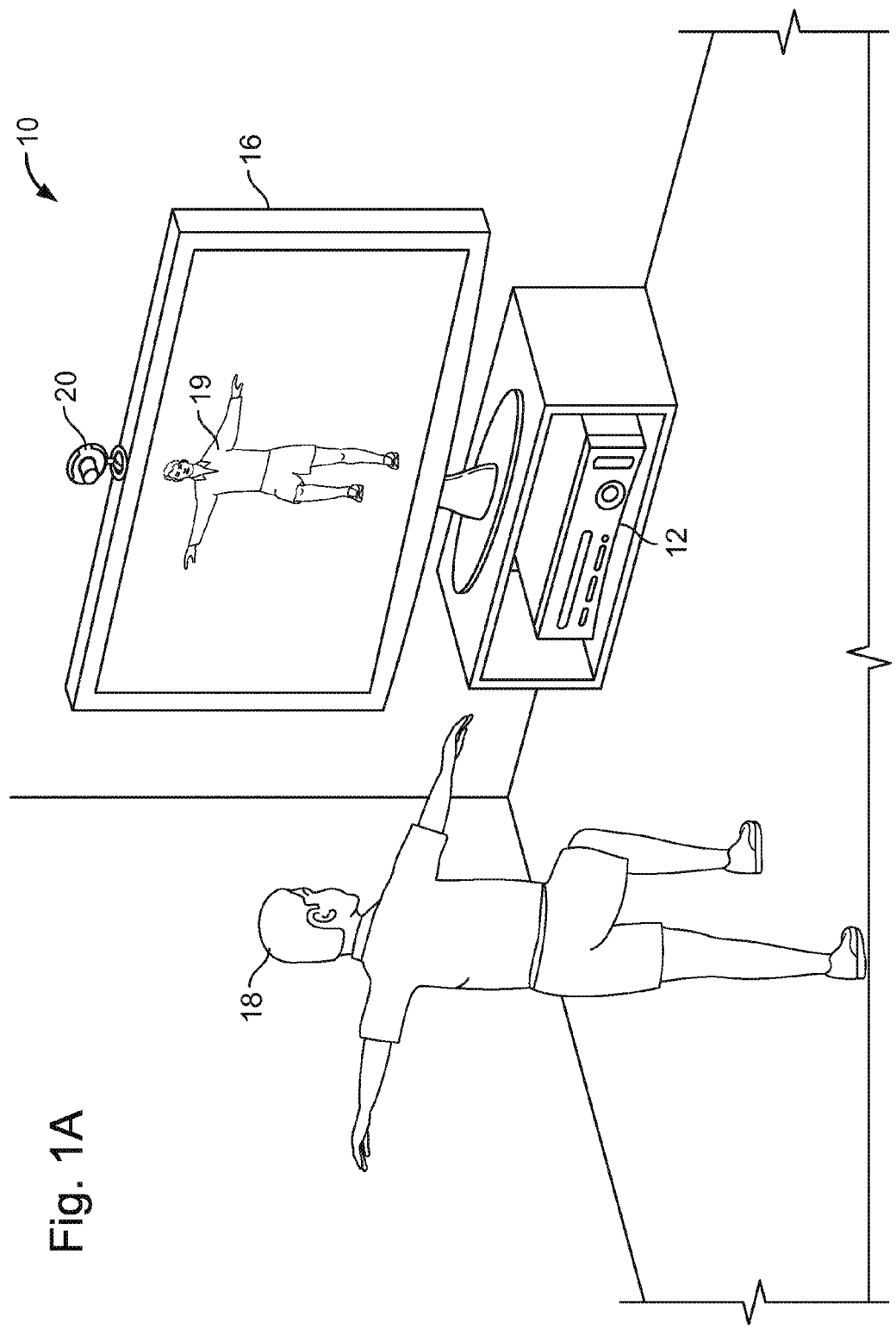
FIG. 1A illustrates an example embodiment of a target recognition, analysis, and tracking system with a user participating in a game or exercise program.
Figure 1B:
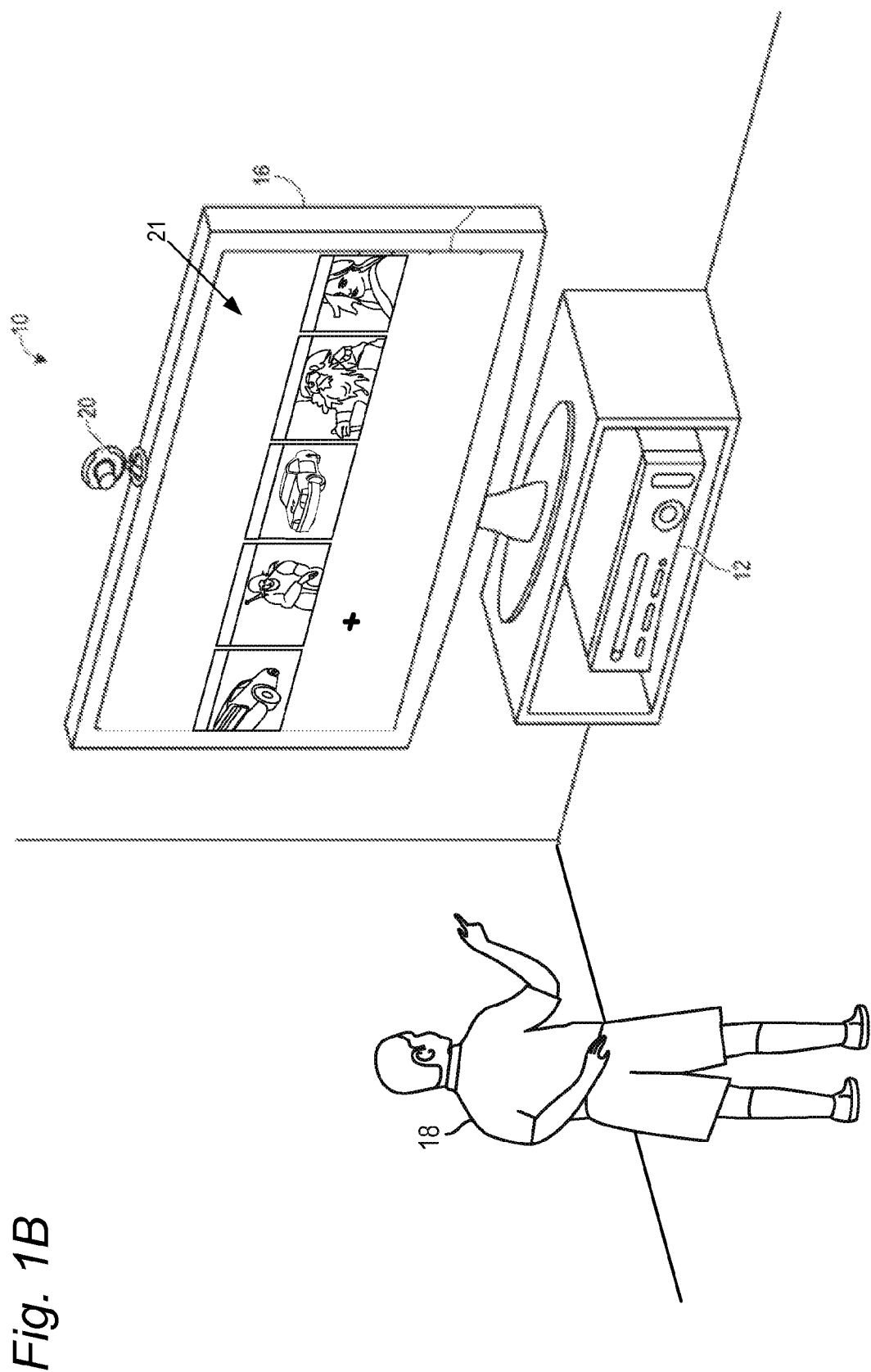
FIG. 1B illustrates an example embodiment of a target recognition, analysis, and tracking system with a user operating a graphical user interface.
Figure 2:
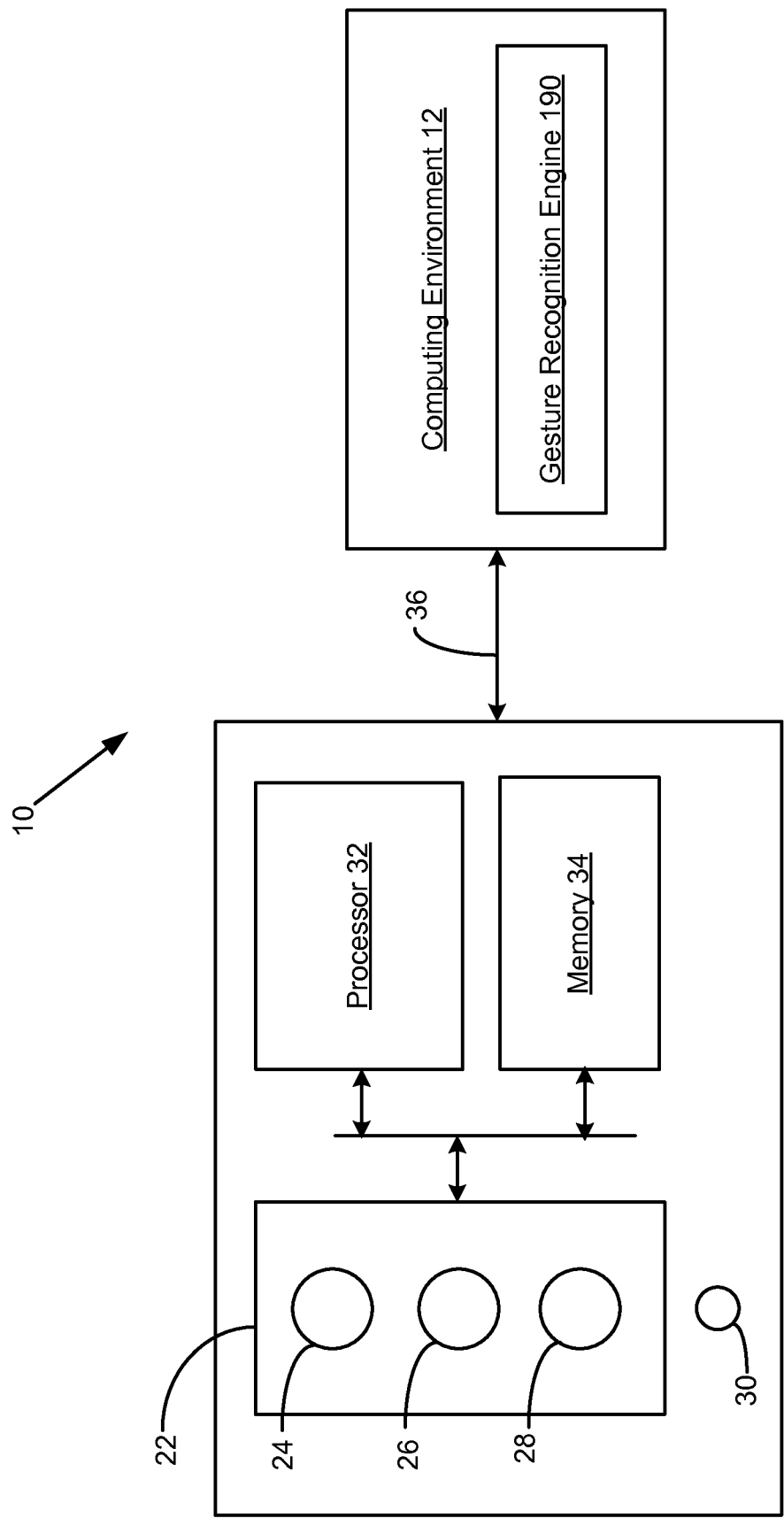
FIG. 2 illustrates an example embodiment of a capture device that may be used in a target recognition, analysis, and tracking system.

Referring initially to FIGS. 1A-2, the hardware for implementing the present technology includes a target recognition, analysis, and tracking system 10 which may be used to recognize, analyze, and/or track a human target such as the user 18. Embodiments of the target recognition, analysis, and tracking system 10 include a computing environment 12 for executing a gaming, exercise or other application, and an audiovisual device 16 for providing audio and visual representations from the gaming, exercise or other application. The system 10 further includes a capture device 20 for detecting position and movement of a user captured by the device 20, which the computing environment receives and uses to control the application. In accordance with the present technology, the position and/or movement data captured by the capture device 20 may further be used by the computing environment 12 to determine the calories burned by the user while interacting with the system 10. Each of these components is explained in greater detail below.

As shown in FIG. 1A, in an example embodiment, the application executing on the computing environment 12 may be an exercise program where user 18 mimics the actions of an on-screen instructor 19 and the present system measures the calories burned by the user in performing the exercises as explained below. However, the present technology may measure caloric burn in any interaction of the user with the system 10. For example, FIG. 1B shows an embodiment where the user 18 is simply interacting with a user interface 21. In further examples, the user may be moving and interacting with the system while playing a game or controlling a gaming or other application. In each of these examples, the system may still measure caloric burn as explained in greater detail below.

In further example embodiments, a user 18 may be holding an object, such as for example a weight. In such embodiments, the system 10 may detect that a user is holding an object and prompt the user to input its weight (or the system may estimate its weight based on its size). Using the weight, the present technology may factor in caloric burn due to the position and/or movement of the object as well as the user's body parts. This is explained in greater detail below.

FIG. 2 illustrates an example embodiment of the capture device 20 that may be used in the target recognition, analysis, and tracking system 10. Further details relating to a capture device for use with the present technology are set forth in copending patent application Ser. No. 12/475,308, entitled "Device For Identifying And Tracking Multiple Humans Over Time," which application is incorporated herein by reference in its entirety. However, in an example embodiment, the capture device 20 may be configured to capture video having a depth image that may include depth values via any suitable technique including, for example, time-of-flight, structured light, stereo image, or the like. According to one embodiment, the capture device 20 may organize the calculated depth information into "Z layers," or layers that may be perpendicular to a Z axis extending from the depth camera along its line of sight.

As shown in FIG. 2, the capture device 20 may include an image camera component 22. According to an example embodiment, the image camera component 22 may be a depth camera that may capture the depth image of a scene. The depth image may include a two-dimensional (2-D) pixel area of the captured scene where each pixel in the 2-D pixel area may represent a length in, for example, centimeters, millimeters, or the like of an object in the captured scene from the camera.

As shown in FIG. 2, according to an example embodiment, the image camera component 22 may include an IR light component 24, a three-dimensional (3-D) camera 26, and an RGB camera 28 that may be used to capture the depth image of a scene. For example, in time-of-flight analysis, the IR light component 24 of the capture device 20 may emit an infrared light onto the scene and may then use sensors (not shown) to detect the backscattered light from the surface of one or more targets and objects in the scene using, for example, the 3-D camera 26 and/or the RGB camera 28.

According to another embodiment, the capture device 20 may include two or more physically separated cameras that may view a scene from different angles, to obtain visual stereo data that may be resolved to generate depth information.

The capture device 20 may further include a microphone 30. The microphone 30 may include a transducer or sensor that may receive and convert sound into an electrical signal. According to one embodiment, the microphone 30 may be used to reduce feedback between the capture device 20 and the computing environment 12 in the target recognition, analysis, and tracking system 10. Additionally, the microphone 30 may be used to receive audio signals that may also be provided by the user to control applications such as game applications, non-game applications, or the like that may be executed by the computing environment 12.

In an example embodiment, the capture device 20 may further include a processor 32 that may be in operative communication with the image camera component 22. The processor 32 may include a standardized processor, a specialized processor, a microprocessor, or the like that may execute instructions that may include instructions for receiving the depth image, determining whether a suitable target may be included in the depth image, converting the suitable target into a skeletal representation or model of the target, or any other suitable instruction.

The capture device 20 may further include a memory component 34 that may store the instructions that may be executed by the processor 32, images or frames of images captured by the 3-D camera or RGB camera, or any other suitable information, images, or the like. According to an example embodiment, the memory component 34 may include random access memory (RAM), read only memory (ROM), cache, Flash memory, a hard disk, or any other suitable storage component. As shown in FIG. 2, in one embodiment, the memory component 34 may be a separate component in communication with the image capture component 22 and the processor 32. According to another embodiment, the memory component 34 may be integrated into the processor 32 and/or the image capture component 22.

As shown in FIG. 2, the capture device 20 may be in communication with the computing environment 12 via a communication link 36. The communication link 36 may be a wired connection including, for example, a USB connection, a Firewire connection, an Ethernet cable connection, or the like and/or a wireless connection such as a wireless 802.11b, g, a, or n connection. According to one embodiment, the computing environment 12 may provide a clock to the capture device 20 that may be used to determine when to capture, for example, a scene via the communication link 36.

Additionally, the capture device 20 may provide the depth information and images captured by, for example, the 3-D camera 26 and/or the RGB camera 28, and a skeletal model that may be generated by the capture device 20 to the computing environment 12 via the communication link 36. A variety of known techniques exist for determining whether a target or object detected by capture device 20 corresponds to a human target. Skeletal mapping techniques may then be used to determine various spots on that user's skeleton, joints of the hands, wrists, elbows, knees, nose, ankles, shoulders, and where the pelvis meets the spine. Other techniques include transforming the image into a body model representation of the person and transforming the image into a mesh model representation of the person.

The skeletal model may then be provided to the computing environment 12 such that the computing environment may perform a variety of actions. In accordance with the present technology, the computing environment 12 may use the skeletal model to determine the calories being burned by the user. Although not pertinent to the present technology, the computing environment may further track the skeletal model and render an avatar associated with the skeletal model on an audiovisual device 16. The computing environment may further determine which controls to perform in an application executing on the computer environment based on, for example, gestures of the user that have been recognized from the skeletal model. For example, as shown, in FIG. 2, the computing environment 12 may include a gesture recognizer engine 190 for determining when the user has performed a predefined gesture.

Figure 3A:
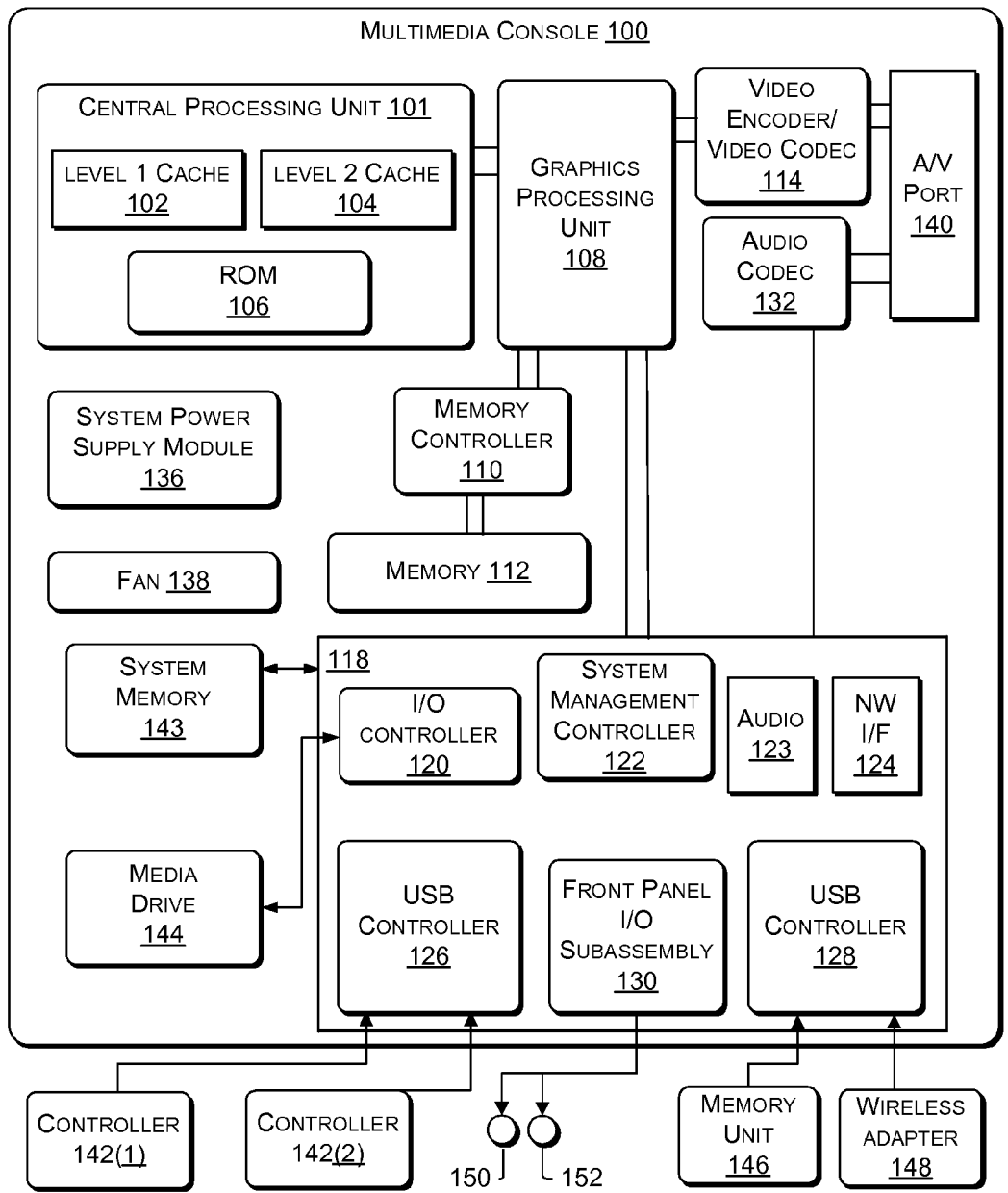
FIG. 3A illustrates an example embodiment of a computing environment that may be used to interpret one or more gestures in a target recognition, analysis, and tracking system.

FIG. 3A illustrates an example embodiment of a computing environment that may be used to interpret one or more positions and motions of a user in a target recognition, analysis, and tracking system. The computing environment such as the computing environment 12 described above with respect to FIGS. 1A-2 may be a multimedia console 100, such as a gaming console. As shown in FIG. 3A, the multimedia console 100 has a central processing unit (CPU) 101 having a level 1 cache 102, a level 2 cache 104, and a flash ROM 106. The level 1 cache 102 and a level 2 cache 104 temporarily store data and hence reduce the number of memory access cycles, thereby improving processing speed and throughput. The CPU 101 may be provided having more than one core, and thus, additional level 1 and level 2 caches 102 and 104. The flash ROM 106 may store executable code that is loaded during an initial phase of a boot process when the multimedia console 100 is powered ON.

A graphics processing unit (GPU) 108 and a video encoder/video codec (coder/decoder) 114 form a video processing pipeline for high speed and high resolution graphics processing. Data is carried from the GPU 108 to the video encoder/video codec 114 via a bus. The video processing pipeline outputs data to an A/V (audio/video) port 140 for transmission to a television or other display. A memory controller 110 is connected to the GPU 108 to facilitate processor access to various types of memory 112, such as, but not limited to, a RAM.

The multimedia console 100 includes an I/O controller 120, a system management controller 122, an audio processing unit 123, a network interface controller 124, a first USB host controller 126, a second USB host controller 128 and a front panel I/O subassembly 130 that are preferably implemented on a module 118. The USB controllers 126 and 128 serve as hosts for peripheral controllers 142(1)-142(2), a wireless adapter 148, and an external memory device 146 (e.g., flash memory, external CD/DVD ROM drive, removable media, etc.). The network interface 124 and/or wireless adapter 148 provide access to a network (e.g., the Internet, home network, etc.) and may be any of a wide variety of various wired or wireless adapter components including an Ethernet card, a modem, a Bluetooth module, a cable modem, and the like.

System memory 143 is provided to store application data that is loaded during the boot process. A media drive 144 is provided and may comprise a DVD/CD drive, hard drive, or other removable media drive, etc. The media drive 144 may be internal or external to the multimedia console 100. Application data may be accessed via the media drive 144 for execution, playback, etc. by the multimedia console 100. The media drive 144 is connected to the I/O controller 120 via a bus, such as a Serial ATA bus or other high speed connection (e.g., IEEE 1394).

The system management controller 122 provides a variety of service functions related to assuring availability of the multimedia console 100. The audio processing unit 123 and an audio codec 132 form a corresponding audio processing pipeline with high fidelity and stereo processing. Audio data is carried between the audio processing unit 123 and the audio codec 132 via a communication link. The audio processing pipeline outputs data to the A/V port 140 for reproduction by an external audio player or device having audio capabilities.

The front panel I/O subassembly 130 supports the functionality of the power button 150 and the eject button 152, as well as any LEDs (light emitting diodes) or other indicators exposed on the outer surface of the multimedia console 100. A system power supply module 136 provides power to the components of the multimedia console 100. A fan 138 cools the circuitry within the multimedia console 100.

The CPU 101, GPU 108, memory controller 110, and various other components within the multimedia console 100 are interconnected via one or more buses, including serial and parallel buses, a memory bus, a peripheral bus, and a processor or local bus using any of a variety of bus architectures. By way of example, such architectures can include a Peripheral Component Interconnects (PCI) bus, PCI-Express bus, etc.

When the multimedia console 100 is powered ON, application data may be loaded from the system memory 143 into memory 112 and/or caches 102, 104 and executed on the CPU 101. The application may present a graphical user interface that provides a consistent user experience when navigating to different media types available on the multimedia console 100. In operation, applications and/or other media contained within the media drive 144 may be launched or played from the media drive 144 to provide additional functionalities to the multimedia console 100.

The multimedia console 100 may be operated as a standalone system by simply connecting the system to a television or other display. In this standalone mode, the multimedia console 100 allows one or more users to interact with the system, watch movies, or listen to music. However, with the integration of broadband connectivity made available through the network interface 124 or the wireless adapter 148, the multimedia console 100 may further be operated as a participant in a larger network community.

When the multimedia console 100 is powered ON, a set amount of hardware resources are reserved for system use by the multimedia console operating system. These resources may include a reservation of memory (e.g., 16 MB), CPU and GPU cycles (e.g., 5%), networking bandwidth (e.g., 8 kbs), etc. Because these resources are reserved at system boot time, the reserved resources do not exist from the application's view.

In particular, the memory reservation preferably is large enough to contain the launch kernel, concurrent system applications and drivers. The CPU reservation is preferably constant such that if the reserved CPU usage is not used by the system applications, an idle thread will consume any unused cycles.

With regard to the GPU reservation, lightweight messages generated by the system applications (e.g., popups) are displayed by using a GPU interrupt to schedule code to render popup into an overlay. The amount of memory required for an overlay depends on the overlay area size and the overlay preferably scales with screen resolution. Where a full user interface is used by the concurrent system application, it is preferable to use a resolution independent of the application resolution. A scaler may be used to set this resolution such that the need to change frequency and cause a TV resynch is eliminated.

After the multimedia console 100 boots and system resources are reserved, concurrent system applications execute to provide system functionalities. The system functionalities are encapsulated in a set of system applications that execute within the reserved system resources described above. The operating system kernel identifies threads that are system application threads versus gaming application threads. The system applications are preferably scheduled to run on the CPU 101 at predetermined times and intervals in order to provide a consistent system resource view to the application. The scheduling is to minimize cache disruption for the gaming application running on the console.

When a concurrent system application requires audio, audio processing is scheduled asynchronously to the gaming application due to time sensitivity. A multimedia console application manager (described below) controls the gaming application audio level (e.g., mute, attenuate) when system applications are active.

Input devices (e.g., controllers 142(1) and 142(2)) are shared by gaming applications and system applications. The input devices are not reserved resources, but are to be switched between system applications and the gaming application such that each will have a focus of the device. The application manager preferably controls the switching of input stream, without knowledge of the gaming application's knowledge and a driver maintains state information regarding focus switches. The cameras 26, 28 and capture device 20 may define additional input devices for the console 100.

Figure 3B:
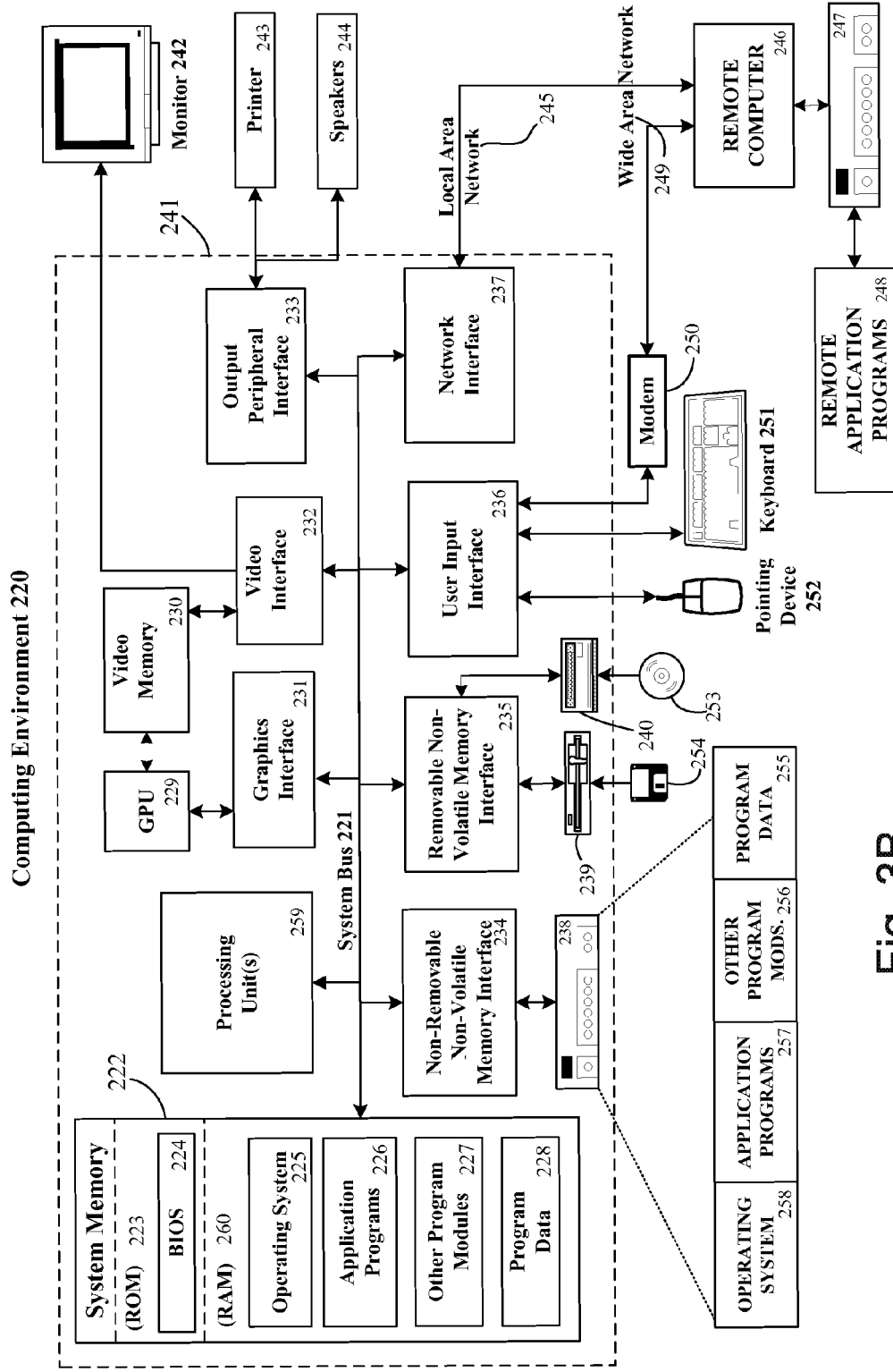
FIG. 3B illustrates another example embodiment of a computing environment that may be used to interpret one or more gestures in a target recognition, analysis, and tracking system.

FIG. 3B illustrates another example embodiment of a computing environment 220 that may be the computing environment 12 shown in FIGS. 1A-2 used to interpret one or more positions and motions in a target recognition, analysis, and tracking system. The computing system environment 220 is only one example of a suitable computing environment and is not intended to suggest any limitation as to the scope of use or functionality of the presently disclosed subject matter. Neither should the computing environment 220 be interpreted as having any dependency or requirement relating to any one or combination of components illustrated in the exemplary operating environment 220. In some embodiments, the various depicted computing elements may include circuitry configured to instantiate specific aspects of the present disclosure. For example, the term circuitry used in the disclosure can include specialized hardware components configured to perform function(s) by firmware or switches. In other example embodiments, the term circuitry can include a general purpose processing unit, memory, etc., configured by software instructions that embody logic operable to perform function (s). In example embodiments where circuitry includes a combination of hardware and software, an implementer may write source code embodying logic and the source code can be compiled into machine readable code that can be processed by the general purpose processing unit. Since one skilled in the art can appreciate that the state of the art has evolved to a point where there is little difference between hardware, software, or a combination of hardware/software, the selection of hardware versus software to effectuate specific functions is a design choice left to an implementer. More specifically, one of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer.

In FIG. 3B, the computing environment 220 comprises a computer 241, which typically includes a variety of computer readable media. Computer readable media can be any available media that can be accessed by computer 241 and includes both volatile and nonvolatile media, removable and non-removable media. The system memory 222 includes computer storage media in the form of volatile and/or nonvolatile memory such as ROM 223 and RAM 260. A basic input/output system 224 (BIOS), containing the basic routines that help to transfer information between elements within computer 241, such as during start-up, is typically stored in ROM 223. RAM 260 typically contains data and/or program modules that are immediately accessible to and/or presently being operated on by processing unit 259. By way of example, and not limitation, FIG. 3B illustrates operating system 225, application programs 226, other program modules 227, and program data 228.

The computer 241 may also include other removable/non-removable, volatile/nonvolatile computer storage media. By way of example only, FIG. 3B illustrates a hard disk drive 238 that reads from or writes to non-removable, nonvolatile magnetic media, a magnetic disk drive 239 that reads from or writes to a removable, nonvolatile magnetic disk 254, and an optical disk drive 240 that reads from or writes to a removable, nonvolatile optical disk 253 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 238 is typically connected to the system bus 221 through a non-removable memory interface such as interface 234, and magnetic disk drive 239 and optical disk drive 240 are typically connected to the system bus 221 by a removable memory interface, such as interface 235.

The drives and their associated computer storage media discussed above and illustrated in FIG. 3B, provide storage of computer readable instructions, data structures, program modules and other data for the computer 241. In FIG. 3B, for example, hard disk drive 238 is illustrated as storing operating system 258, application programs 257, other program modules 256, and program data 255. Note that these components can either be the same as or different from operating system 225, application programs 226, other program modules 227, and program data 228. Operating system 258, application programs 257, other program modules 256, and program data 255 are given different numbers here to illustrate that, at a minimum, they are different copies. A user may enter commands and information into the computer 241 through input devices such as a keyboard 251 and a pointing device 252, commonly referred to as a mouse, trackball or touch pad. Other input devices (not shown) may include a microphone, joystick, game pad, satellite dish, scanner, or the like. These and other input devices are often connected to the processing unit 259 through a user input interface 236 that is coupled to the system bus, but may be connected by other interface and bus structures, such as a parallel port, game port or a universal serial bus (USB). The cameras 26, 28 and capture device 20 may define additional input devices for the console 100. A monitor 242 or other type of display device is also connected to the system bus 221 via an interface, such as a video interface 232. In addition to the monitor, computers may also include other peripheral output devices such as speakers 244 and printer 243, which may be connected through an output peripheral interface 233.

The computer 241 may operate in a networked environment using logical connections to one or more remote computers, such as a remote computer 246. The remote computer 246 may be a personal computer, a server, a router, a network PC, a peer device or other common network node, and typically includes many or all of the elements described above relative to the computer 241, although only a memory storage device 247 has been illustrated in FIG. 3B. The logical connections depicted in FIG. 3B include a local area network (LAN) 245 and a wide area network (WAN) 249, but may also include other networks. Such networking environments are commonplace in offices, enterprise-wide computer networks, intranets and the Internet.

When used in a LAN networking environment, the computer 241 is connected to the LAN 245 through a network interface or adapter 237. When used in a WAN networking environment, the computer 241 typically includes a modem 250 or other means for establishing communications over the WAN 249, such as the Internet. The modem 250, which may be internal or external, may be connected to the system bus 221 via the user input interface 236, or other appropriate mechanism. In a networked environment, program modules depicted relative to the computer 241, or portions thereof, may be stored in the remote memory storage device. By way of example, and not limitation, FIG. 3B illustrates remote application programs 248 as residing on memory device 247. It will be appreciated that the network connections shown are exemplary and other means of establishing a communications link between the computers may be used.

Figure 4:
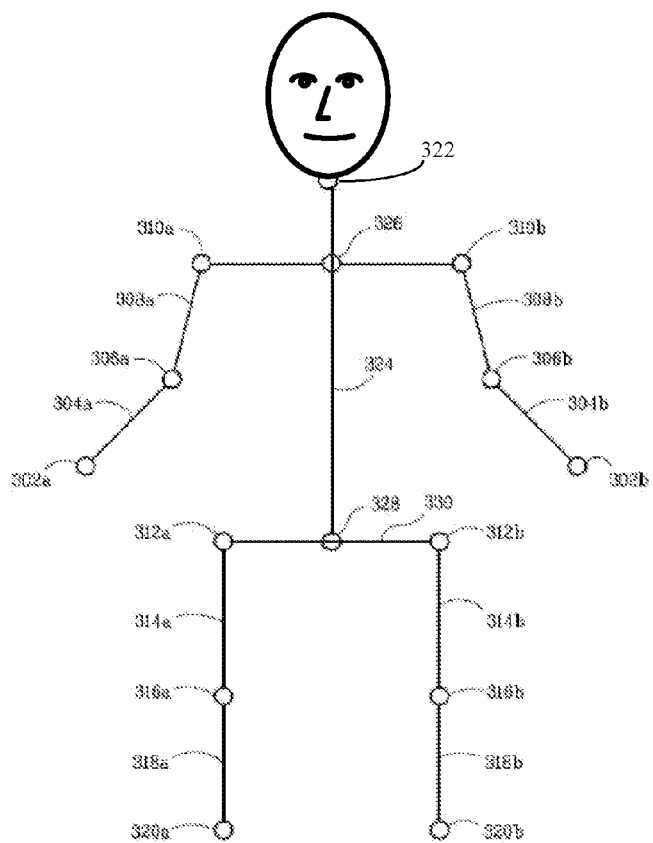
FIG. 4 illustrates a skeletal mapping of a user that has been generated from the target recognition, analysis, and tracking system of FIG. 2.

FIG. 4 depicts an example skeletal mapping of a user that may be generated from the capture device 20. In this embodiment, a variety of joints and bones are identified: each hand 302, each forearm 304, each elbow 306, each bicep 308, each shoulder 310, each hip 312, each thigh 314, each knee 316, each foreleg 318, each foot 320, the head 322, the torso 324, the top 326 and the bottom 328 of the spine, and the waist 330. Where more points are tracked, additional features may be identified, such as the bones and joints of the fingers or toes, or individual features of the face, such as the nose and eyes.

Figure 5:
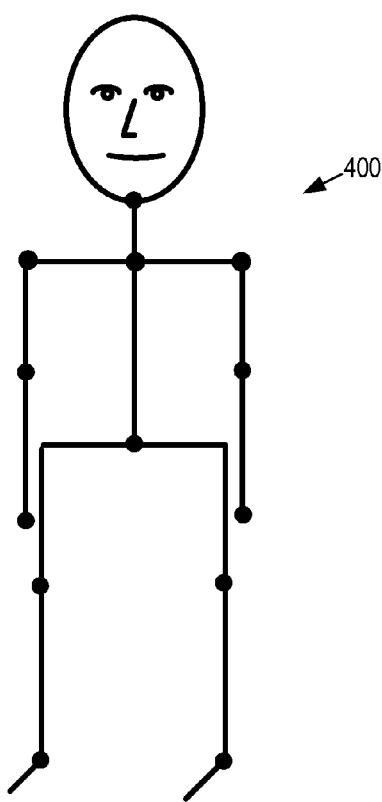
FIG. 5 shows a representation of a user standing in a neutral position.
Figure 9:
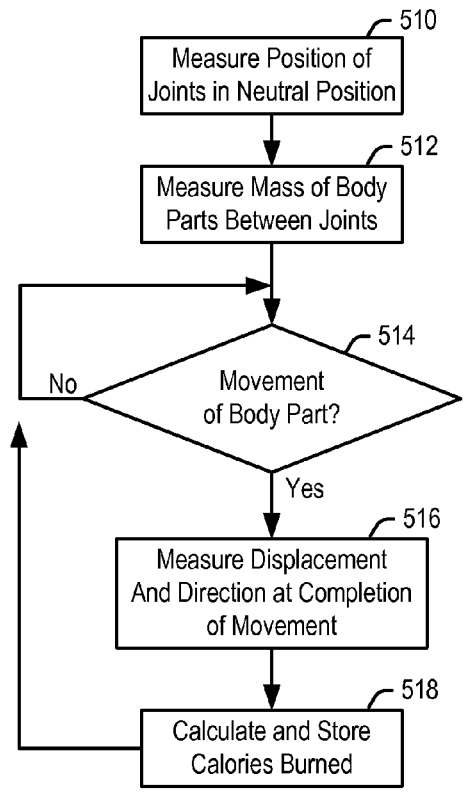
FIG. 9 is a flowchart for determining caloric burn according to a second embodiment of the system.
Figure 10:
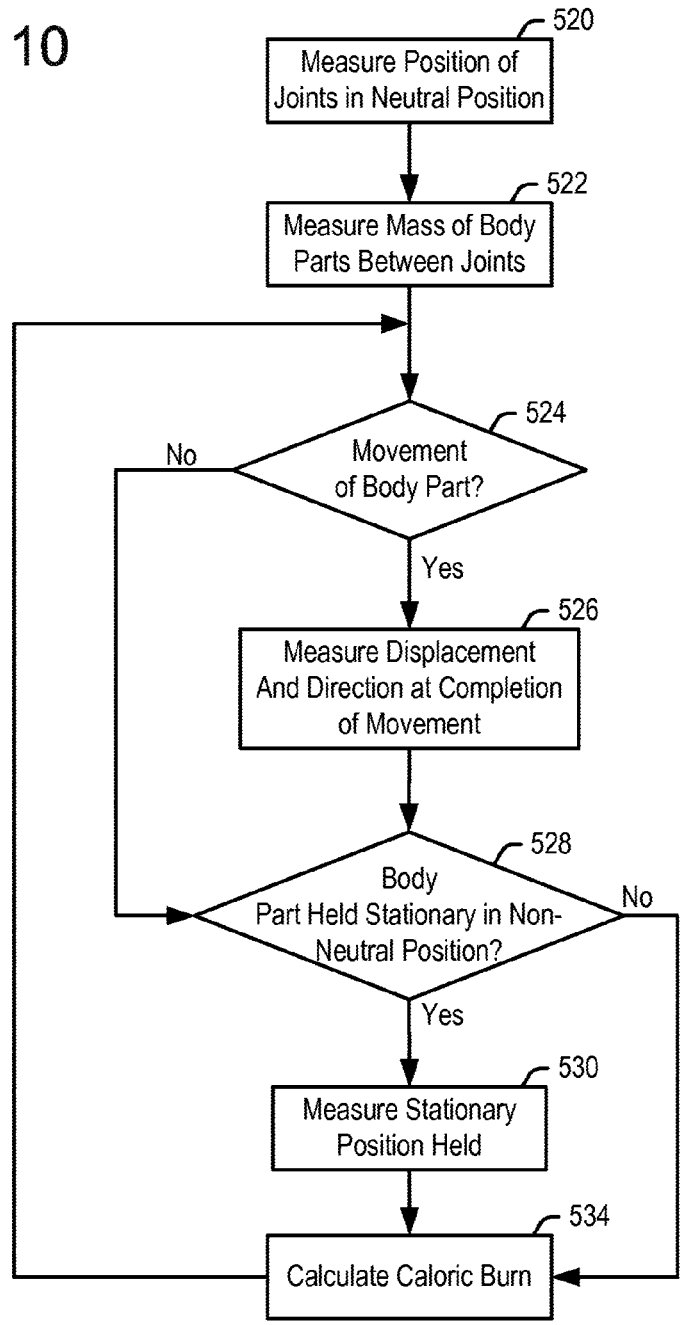
FIG. 10 is a flowchart for determining caloric burn according to a third embodiment of the system.

Embodiments of the present technology will now be explained with reference to the illustrations of FIGS. 5 through 7 and the flowcharts of FIGS. 8 through 10. FIG. 5 shows a user 400 within the field of view of capture device 20 standing in a neutral position, i.e., at rest while the body is standing erect. Some muscle work is being performed while standing, but this work may be omitted in embodiments. In further embodiments, some base amount of work may be measured and stored while a user is standing at rest. There may be other neutral positions where the body is at rest, such as for example where the user is seated or where the user is lying flat on the ground.

Figure 7:
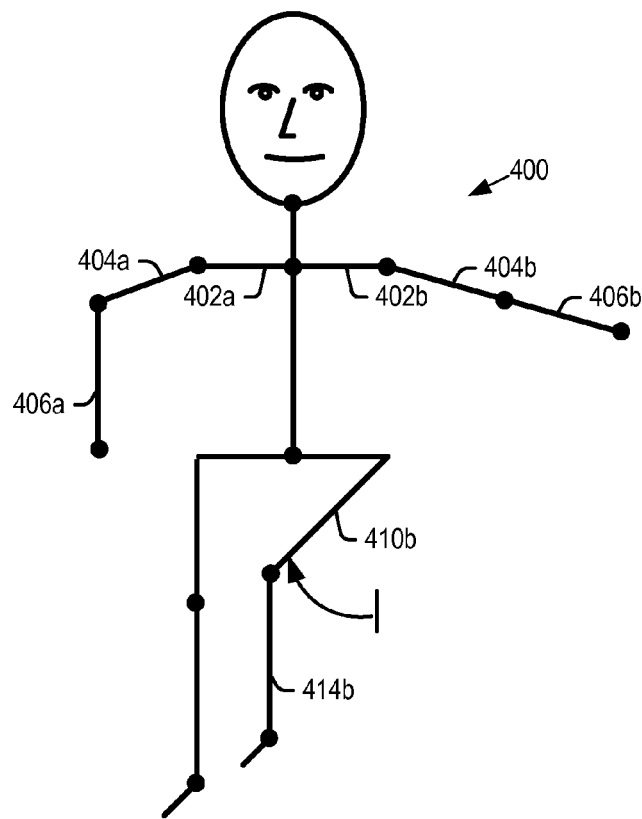
FIG. 7 shows a representation of a user with arms and legs moved to non-neutral positions.
Figure 8:
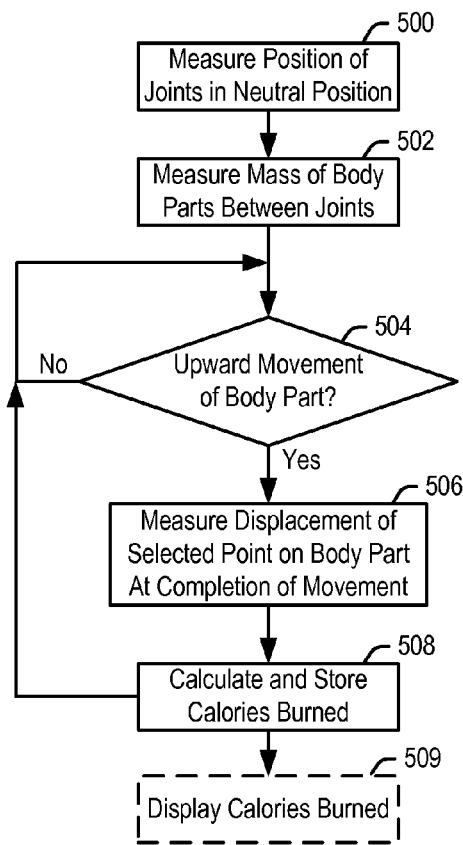
FIG. 8 is a flowchart for determining caloric burn according to a first embodiment of the system.

FIG. 8 describes a straightforward embodiment of the present technology. In a step 500, the processor (within computing device 12 or possibly within capture device 20) determines a reference position of each joint of the user 400 in the neutral position. In step 502, the processor determines a mass of the body parts between the joints. This may be done a number of ways. In one embodiment, the system measures a thickness, or volume, of the different body parts from the 3-D images of the body parts captured by the capture device 20 (the mass of a user's body parts is not shown in FIGS. 5-7). In this way, the volume for upper and lower arms, upper and lower legs, and torso may be determined. The mass of a user's hands, feet, head and neck may also be determined in further embodiments. The volume determined for each body part may then be multiplied by some constant derived value to result in a mass for each body part. As clothes may at times make the volumetric determination difficult, the measurement may be taken over time for the different body parts, and the results fine tuned for each.

Figure 6:
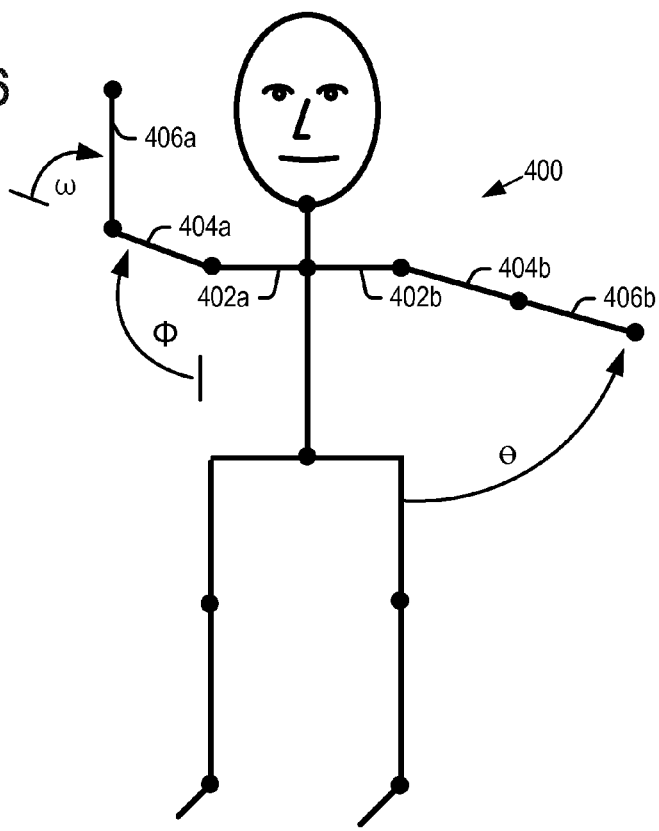
FIG. 6 shows a representation of a user with arms moved to non-neutral positions.

Referring now to FIG. 6, the user 400 has raised both arms. The user has raised his left arm from his side straight up from the shoulder 402b, keeping his elbow straight so that the lower arm 406b extends generally straight from the upper arm 404b. The user has raised his right arm from his side, but has also raised his lower arm 406a with respect to his upper arm 404a by bending at the elbow. It is understood that the movements indicated in FIG. 6 are by way of example only, and the user may move any of his body parts in a variety of ways and be measured as described below. FIG. 7 is a further example of movement, where the user has moved both his arms and his legs. As explained below, the present technology measures caloric burn as an aggregate of caloric burn attributable to each body part. In further embodiments, it is contemplated that body parts may be combined together (resulting in a mass of the constituent body parts), and caloric burn be calculated based on the combined body parts.

In the straightforward embodiment of FIG. 8, the system next checks in step 504 whether a body part was moved upward, i.e., against the force of gravity. The system measures this on a body part-by-body part basis. One way the system may make this measurement is by measuring a change in joint angle. Thus, the system may first check for movement of body parts closest to the torso (though it may be otherwise in alternative embodiments). It may determine that the left shoulder joint has rotated upward an angle $\theta$ and determine that the elbow joint has not rotated. From this determination, the system is able to determine how high the user has lifted both his upper arm 404b and his lower arm 406b. Similarly, the system may determine that the user has lifted his right upper arm through an angle $\Phi$ at the shoulder joint, and raised his lower arm an angle $\omega$ at the elbow joint. Again, from this information, the system is able to determine how high the user has lifted both his upper arm 404a and his lower arm 406a.

Once the system determines a body part has moved upward in step 504 as described above, the system may then pick an arbitrary point, for example the distal most joint on each body part and measure its upward displacement once the upward movement is finished in step 506. The distal most point of the upper arm would be the elbow joint, the distal most point on the lower leg would be the ankle joint, etc. The system would then calculate the displacement of that point for a given body part that moves upward in step 506.

In step 508, given the calculated mass and upward displacement, the system then calculates the calories burned due to upward movement of a given body part. The system may use the following relationships for calculating energy burned by a moving mass in joules:

$$\text{joules} = \text{mass} \times \text{gravity} \times \text{upward displacement}$$

Muscles are only on average 15-25% efficient. The extra energy is lost as heat. Thus, assuming 20% efficiency, the caloric energy burn is given in joules by:

$$\text{joules}=\text{mass}\times\text{gravity}\times\text{displacement}\times(100/20)$$

It is understood that some corrective factor other than 20% may be used, such as for example any factor between 15% and 25%. The limits may be above and/or below this range in further embodiments. Joules may be converted to calories by:

$$1 \text{ calorie}=4184 \text{ joules.}$$

The calories burned due to the movement of a given body part are calculated and stored in step 508. The system performs the above steps 500 through 508 repeatedly to keep a running total of calories burned based on movement of different body parts. The running total may optionally be displayed to a user in step 509 (shown in dashed lines to indicate the step may be skipped in further embodiments). The running total may be given per unit time, to for example show the calories burned per minute for the users movements.

Thus, referring again to FIG. 6, taking volumetric measurements, the system may determine the mass of the user's body parts, including the following:

Upper right arm: 1.88 kg
Lower right arm: 1.51 kg
Upper left arm: 1.86 kg
Lower left arm: 1.50 kg In embodiments, the system may include a determined mass of the user's hands as part of the lower arms. In further embodiments, the mass of the hands may be separately calculated and used, or the mass of the hands may be omitted.

The system may further determine that the user's arms in this example moved upward by the following displacements.

Upper right arm: 0.4 m
Lower right arm: 1.2 m
Upper left arm: 0.4 m
Lower left arm: 0.6 m The system would then perform the calculation on the different body parts, each separately:

$$\text{Calories burned upper right arm}=\text{mass}\times\text{gravity}\times\text{disp.}\times(100/20)/4184$$

$$\text{Calories burned upper right arm}=1.88\times9.82\times0.4(100/20)/4184$$

$$\text{Calories burned upper right arm}=0.0088 \text{ calories}$$

The same calculations may be performed on the other arm portions, so that the movements shown in FIG. 6 result in the following caloric burns:

Calories burned upper right arm=0.0088 calories
Calories burned lower right arm=0.0212 calories
Calories burned upper left arm=0.0087 calories
Calories burned lower left arm=0.0106 calories
Total calories burned from the movement shown in FIG. 6: 0.0493

The same calculations would be performed if a user lifted his leg(s), as shown in FIG. 7. Moreover, the calculation is not always made relative to a neutral position. For example, if a user was bent over, once the user straightened up to the neutral position, this upward movement of the torso, upper arms, etc., would result in work and calories burned as described above.

The above embodiment represents a straightforward calculation of calories burned based on the upward movement of body parts against gravity. However, a user may also be burning calories when moving body parts downward (in a controlled muscle movement) and/or horizontally. FIG. 9 is a flowchart of a further embodiment taking into consideration caloric burn in these situations as well. FIG. 9 shows similar steps to FIG. 8, including measuring joints at a neutral position in step 510 and measuring mass of body parts in step 512. In step 514, the embodiment of FIG. 9 measures any movement of body parts. Again this may be accomplished by detecting changes in joint angle.

In step 516, both the displacement and direction of movement may be measured as a vector quantity, upon detecting that a movement has been completed. As above, this may be measured using an arbitrary point on a body part, such as for example a most distal point on the body part. In step 518, the calories burned by the movement of respective body parts is determined. In this embodiment, a direction factor normalized between some lower limit and 1 may be calculated and factored into the equations for calculating calories burned for a given body part. Thus, calories burned in this embodiment are given by:

$$\text{Calories burned}=\text{mass}\times\text{gravity}\times\text{displacement}\times(100/20)\times df/4184$$

where df is the direction factor. In this equation, displacement is absolute displacement, not merely vertical displacement.

For pure upward vertical displacement, df may be equal to 1, thus resulting in the same calculations as set forth above with respect to FIG. 8. As the movement becomes less vertical and more horizontal, the direction factor may decrease. Thus, while the absolute displacement of a body part may be the same as between a pure vertical motion and a motion including vertical and horizontal components, the amount of calories burned for a combined vertical/horizontal motion will be less than the calories burned for a pure vertical motion. Moreover, a pure horizontal displacement of a body part will have the above-identified calculation of calories multiplied by some determined direction factor df<1. Thus, unlike the embodiment of FIG. 8, the embodiment of FIG. 9 will include caloric burn for horizontal motions. It may for example be some arbitrarily selected value such that 0<df<1.

Similarly, for movements between vertically upward and horizontal, the direction factor may decrease from 1 to the selected value at horizontal. The direction factor for these intermediate positions may decrease linearly, or according to a determined trigonometric function depending on the vector angle of the displacement.

Likewise, when a user is lowering a body part, such as dropping an arm down back to the neutral position, this movement may still be burning calories. As such, the direction factor will have some non-zero value, but less than the value used for pure horizontal motion.

In further embodiments, the velocity with which a user moves a body part may also be factored into the equation. Thus for example, a velocity factor may also be provided in either of the above-described calculations of calories (in FIG. 8 and in FIG. 9). This velocity factor may increase the amount of calories burned for faster motions.

In the above-described embodiments, caloric burn is measured in part as a function of displacement. However, a body part in a fixed position, for example an extended arm or leg, may also be burning calories. Accordingly, a further embodiment described with respect to FIG. 10 takes into account caloric burn due to movement and body parts held stationary in a non-neutral position. As in the above embodiments, the system initially measures joints at a neutral position in step 520 and measures mass of body parts in step 522. In step 514, the embodiment of FIG. 9 measures any movement of body parts. Again this may be accomplished by detecting changes in joint angle. If movement is detected, the system measures the displacement and direction as a vector quantity as described above with respect to FIG. 9. Step 526 may alternatively consider only upward vertical motion as described in the embodiment of FIG. 8.

After step 526, or after step 524 if no motion is detected, the system of this embodiment next checks whether a body part is held stationary in a non-neutral position in step 528. As noted above, when in the neutral position, a stationary body part is either not burning calories or may be assigned some small constant. However, when stationary in a non-neutral position, the body part is burning calories. Thus, in this embodiment, the system measures the stationary position held and the length of time it is held for in step 530.

In step 534, the system determines the caloric burn. This determination may include a determination of caloric burn according any of the above described embodiments, plus caloric burn due to any measured stationary, non-neutral body part position. Different equations may be used to calculate caloric burn due to stationary, non-neutral body position. In embodiments, the caloric burn may be a function of the potential energy stored in a body part. This potential energy will be a function of its mass, as measured in step 522, gravity and its position relative to neutral. In one embodiment for example, a leg or arm held straight out along a horizontal from the torso will have a higher potential energy than a leg or arm held out at some angle other than 90°. Thus, the amount of calories burned will be higher for a leg or arm held straight out as opposed to a leg or arm held out at some non orthogonal angle.

It may happen that a body part, held stationary at some non-neutral position, burns more calories per unit time the longer it is held out there, due to the increase in strain on the muscle. As such, the caloric burn calculated in an alternative embodiment may also factor in time and the caloric burn for a give unit of time may increase the longer the body part is held at that position.

The above-described embodiments set forth methods of measuring caloric burn when body parts are moved or held at a non-neutral position such as shown in FIGS. 6 and 7. However, when a user's legs remain on the ground and a user squats (i.e., bends his knee or knees), this presents a special situation. In particular, the mass that is used for measuring caloric burn of the legs which remain on the ground in this case is not just the mass of the user's legs. The leg(s) on the ground are in fact supporting the user's entire body weight, and as such, the user's entire mass may be factored into the equation for caloric burn in this instance. Thus, in this embodiment, the system may calculate caloric burn according to any of the above-described embodiments. However, in this embodiment, the mass used for the upper or lower legs that remain on the ground during the squat will be increased to include the user's entire mass.

The capture device 20 of the present system is able to determine when a user is squatting and whether the squat involves both the user's legs on the ground supporting the user's weight, or whether the user is supporting his weight on just one leg (with for example the opposite weight being held off the ground). In this case, the system may add to the mass of the user's leg(s) the user's mass from all body parts other than a user's legs. This mass may be apportioned between both lower legs and both upper legs (where the user has both feet on the ground), or between one lower leg and one upper leg (where the user has only that one leg on the ground). With this apportionment, the system may calculate caloric burn due to the squat according to any of the above-described embodiments.

Figure 11:
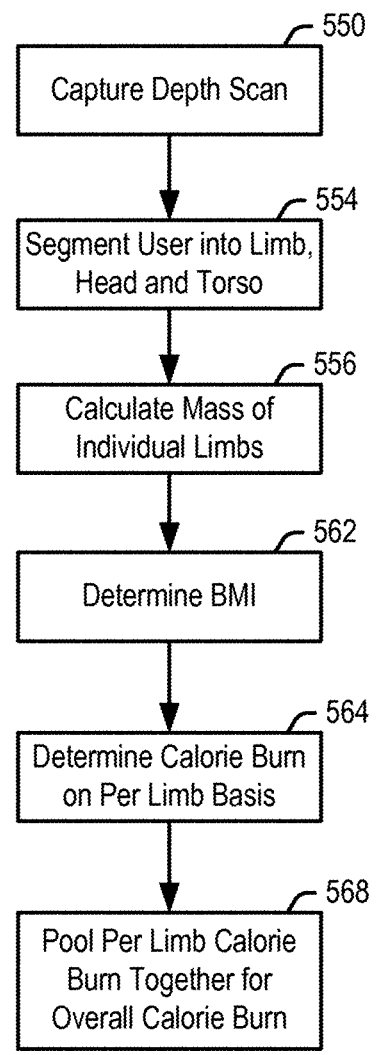
FIG. 11 is a flowchart for determining caloric burn according to a fourth embodiment of the system.

FIG. 11 shows a further embodiment of the present technology where calorie burn is determined by determining a user's weight on a per limb basis and a BMI (body mass index) for a user. BMI is a statistical measure of body weight, which in embodiments is based on a user's weight and height. In step 550, a depth scan may be taken. In this and the other embodiments described above, a user may be prompted to wear tight clothing to allow for the best estimate of a user's weight. The tight clothing allows assumptions that what is detected in the depth scan is the actual size and shape of the user's body. In this and the other embodiments, the user may also be prompted to face the capture device 20 and to do a quarter, half and/or full turn from that position, again so that the capture device can get a full view of the user's physique to allow the best estimate of body weight.

In step 554, a user's body is segmented into different parts, for example, the limbs, head and torso. By taking the silhouette of the player from the depth scan, and superimposing the captured data over the known skeleton for the user, this allows segmentation of each limb, the head and torso for the user.

From step 554, a mass of each of user's limbs may be calculated in step 556. Each limb can be modeled in a volumetric pixel grouping, or voxel group, in 3-D space. The known surface area of each limb obtained from the scan of step 550 can be doubled, as most people are cylindrical. This method may also be used in any of the above-described embodiments. Using figures of known density for different limbs, the mass of each limb can then be determined. This may also be used to determine the mass of a user's torso. In embodiments where the system is able to distinguish head from hair, this may also be used to determine the mass of a user's head. The weight of a user's limbs, torso and/or head may also be determined from the mass calculation by the equation weight=mass×gravity.

Taking the weight of individual limbs, torso and/or head, an approximation of BMI for the user may be determined in step 562. BMI is a function of both weight and height. A user's height may be determined in the scan of step 550, or a user may be prompted to manually enter their height. In further embodiments, a user may be prompted to enter their weight, which may also then be used in determining the weight of a user's limbs, torso and/or head.

With a user BMI and per limb weight known, caloric burn may then be calculated on a per limb basis in step 564. This may be performed on a per limb basis under any of the embodiments described above, using the specific weight of a limb. The size of a limb may also be factored in, by determining the area over which the weight is distributed, to provide a pressure exerted on the limb.

Step 554 may calculate the calories burned by a moving limb per any of the above-described embodiments, and using the weight of a limb and/or pressure on the limb as determined in the current embodiment. Moreover, the scan in step 550 is able to determine when one or more limbs are in a non-neutral position. Using a known deviation away from neutral for a given limb, and the weight of that limb and/or pressure on that limb, the system is able to determine the calories burned by that limb over the time the user is in the non-neutral position. Thus, the system is able to determine calorie burn while a person is standing still, but for example has a leg or arm lifted.

In step 568, the system sums the calorie burn determined for all limbs to provide an overall calorie burn. In this embodiment, different users performing the same movements and/or static, non-neutral positions may burn different amounts of calories. This is because the system has calculated the weight of a this specific user's limbs, torso, etc., and that specific weight is used in calculating weight burn. The weight calculation for a given limb may and likely will vary between different users.

The foregoing detailed description of the inventive system has been presented for purposes of illustration and description. It is not intended to be exhaustive or to limit the inventive system to the precise form disclosed. Many modifications and variations are possible in light of the above teaching. The described embodiments were chosen in order to best explain the principles of the inventive system and its practical application to thereby enable others skilled in the art to best utilize the inventive system in various embodiments and with various modifications as are suited to the particular use contemplated. It is intended that the scope of the inventive system be defined by the claims appended hereto.

What is claimed:

1. In a system including a computing environment coupled to a capture device for capturing user motion, a method of determining caloric burn of a user of the system, comprising:
   a) capturing an image of a body part of a user via the capture device;
   b) determining a mass of the body part captured in said step a) via a processor of the computing environment using the image of the body part captured in said step a);
   c) capturing a movement of the body part via the capture device; and
   d) determining calories burned by the body part due to the captured movement of the body part in said step c) and the mass of the body part determined in said step b).

2. The method of claim 1, further comprising the step of displaying the calories burned as determined in said step d) via a display associated with the computing environment.

3. The method of claim 1, said step d) comprising the step of determining calories burned based on an upward movement of the body part.

4. The method of claim 1, said step d) comprising the step of determining calories burned based on at least one of a vertical movement, a horizontal movement, and a combination of vertical and horizontal movements.

5. The method of claim 1, said step d) comprising the step of determining calories burned based on maintaining a body part in a stationary, non-neutral position.

6. The method of claim 1, further comprising the step of performing the movement of the body part in response to one of an exercise application and a gaming application program displayed on a display associated with the computing environment.

7. The method of claim 1, said step b) of determining the mass of a body part performed by segmenting a user into limbs, head and torso from the scan of step a), determining a 3-D voxel group for a given limb, and determining a mass of the given limb based on the voxel group and a known density of the given limb.

8. The method of claim 1, said step b) of determining the mass of a body part performed by using a determined volume of the body part.

9. The method of claim 1, further comprising the step of calculating caloric burn of a user by calculating and summing caloric burn due to movement of arms, legs and torso.

10. The method of claim 9, further comprising the step of storing a running total of caloric burn of a user over one or more discrete time intervals.

11. A system, comprising:
   a capture device capable of capturing an image of one or more discrete body parts of a user as the user moves within a field of view of the capture device; and
   a computing environment associated with the capture device, the computing environment including a processor capable of calculating a mass of the one or more discrete body parts by a volume of the one or more body parts from one or more 3-D images of the one or more body parts captured by the capture device, and determining calories burned by the one or more discrete body parts due to the determined mass of the one or more discrete body parts and a direction and degree of movement of the one or more discrete body parts.

12. The system of claim 11, the computing environment further comprising storage for storing an aggregate total of the calories burned by the one or more discrete body parts over a period of time.

13. The system of claim 11, the computing environment calculating calories burned by one or more discrete body parts based on at least one of an upward movement of a body part, a downward movement of a body part, a horizontal movement of a body part and a combination of vertical and horizontal movements of a body part.

14. The system of claim 13, the computing environment further calculating calories burned by one or more discrete body parts based on a velocity of movement of the body part.

15. The system of claim 11, further comprising a display associated with the computing environment, the display displaying movements of the user and displaying the calories burned as determined by the processor.

16. The system of claim 11, the processor determining caloric burn of a body part when the body part moves from a neutral position to a non-neutral position, when the body part moves to a neutral position from a non-neutral position and when the body part is held in a non-neutral position.

17. A system for facilitating weight loss, comprising:
   a capture device capable of capturing an image of one or more discrete body parts of a user as the user moves within a field of view of the capture device;
   a computing environment associated with the capture device, the computing environment including determining a mass of the one or more discrete body parts captured by the capture device, and determining calories burned by the one or more discrete body parts due to the determined mass of the one or more discrete body parts and a direction and degree of movement of the one or more discrete body parts, the processor further running an exercise program; and
   a display associated with the computing environment, the display prompting a user to perform exercises per the exercise program run by the processor, the display further displaying the calories burned as determined by the processor.

18. The system of claim 17, the computing environment calculating calories burned by one or more discrete body parts based on determined masses of the one or more discrete body parts, gravity, displacements of the one or more body parts and directions of displacements of the one or more body parts.

19. The system of claim 18, the computing environment further calculating calories burned by one or more discrete body parts based on a potential energy stored in one or more discrete body parts relative to a neutral position.

20. The system of claim 17, wherein the exercise program running on the computing environment causes the display to display an image of a person performing exercises that the user is supposed to mimic in order to burn calories.

21. A system, comprising:
   a capture device capable of capturing an image of a user as the user moves within a field of view of the capture device; and
   a computing environment associated with the capture device, the computing environment including a processor capable of segmenting the user into limbs, head and torso from the image of the user, determining a 3-D voxel group for a given limb, determining a mass of the given limb based on the voxel group and a known density of the given limb, and determining calories burned by the one or more discrete body parts due to the determined mass of the one or more discrete body parts and a direction and degree of movement of the one or more discrete body parts.

22. The system of claim 21, the computing environment further comprising storage for storing an aggregate total of the calories burned by the one or more discrete body parts over a period of time.

23. The system of claim 21, further comprising a display associated with the computing environment, the display displaying movements of the user and displaying the calories burned as determined by the computing environment.

* * * * *